United States Patent
Brown et al.

(10) Patent No.: US 12,285,602 B2
(45) Date of Patent: *Apr. 29, 2025

(54) METHODS OF TREATING DISEASE USING AURICULAR PERIPHERAL NERVE FIELD STIMULATION

(71) Applicant: NEURAXIS, INC., Versailles, IN (US)

(72) Inventors: Christopher R. Brown, Greensburg, IN (US); Gary M. Peterson, Versailles, IN (US)

(73) Assignee: NEURAXIS, INC., Verasilles, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/377,968

(22) Filed: Oct. 9, 2023

(65) Prior Publication Data
US 2024/0033505 A1    Feb. 1, 2024

Related U.S. Application Data

(63) Continuation of application No. 17/725,761, filed on Apr. 21, 2022, now Pat. No. 11,813,448, which is a (Continued)

(51) Int. Cl.
*A61N 1/05* (2006.01)
*A61N 1/36* (2006.01)
*A61K 31/485* (2006.01)

(52) U.S. Cl.
CPC ......... *A61N 1/0529* (2013.01); *A61N 1/0551* (2013.01); *A61N 1/36071* (2013.01); *A61N 1/36096* (2013.01); *A61K 31/485* (2013.01)

(58) Field of Classification Search
CPC ................ A61N 1/0529; A61N 1/0551; A61N 1/36071; A61N 1/36036; A61K 31/485
See application file for complete search history.

(56) References Cited

U.S. PATENT DOCUMENTS

| 4,305,402 A | 12/1981 | Katims |
| 4,646,744 A | 3/1987 | Capel |

(Continued)

FOREIGN PATENT DOCUMENTS

| AT | 395108 B | 9/1992 |
| EP | 2474339 A1 | 7/2012 |

(Continued)

OTHER PUBLICATIONS

Non-Final Office Action dated Mar. 19, 2018 filed in U.S. Appl. No. 10/010,479 issued Jul. 3, 2018.

(Continued)

*Primary Examiner* — Catherine M Voorhees
(74) *Attorney, Agent, or Firm* — Barnes & Thornburg LLP

(57) ABSTRACT

A method for treating pain or discomfort in a patient is disclosed. The method comprises stimulating a cranial nerve with an electrical signal. The pain or discomfort may be a withdrawal symptom. The cranial nerve may be in an auricular area of the patient. The cranial nerve may be cranial nerve V, cranial nerve VII, cranial nerve IX, cranial nerve X, or branches of greater and lesser occipital nerves thereof and their associated neurovascular bundles. The withdrawal symptom may result from cessation of an opioid. The method may further comprise administering a secondary drug treats one or more of the withdrawal symptoms and addiction. The secondary drug may be administered about one day to about one week after initiating the stimulating step.

12 Claims, 3 Drawing Sheets

Related U.S. Application Data continuation of application No. 16/534,159, filed on Aug. 7, 2019, now Pat. No. 11,331,473, which is a continuation of application No. 15/488,416, filed on Apr. 14, 2017, now Pat. No. 10,413,719.

(60) Provisional application No. 62/324,598, filed on Apr. 19, 2016, provisional application No. 62/323,369, filed on Apr. 15, 2016.

(56) References Cited

U.S. PATENT DOCUMENTS

| | | | |
|---|---|---|---|
| 4,865,048 A | 9/1989 | Eckerson | |
| 5,084,007 A | 1/1992 | Malin | |
| 5,458,625 A | 10/1995 | Kendall | |
| 6,212,433 B1 | 4/2001 | Behl | |
| 6,296,652 B1 | 10/2001 | Qingmin | |
| 7,092,849 B2 | 8/2006 | Lafitte et al. | |
| 8,428,719 B2 | 4/2013 | Napadow | |
| 8,761,872 B2 | 6/2014 | Hinrichsen et al. | |
| 9,662,269 B2 | 5/2017 | Brown et al. | |
| 9,839,577 B2 | 12/2017 | Brown et al. | |
| 10,010,479 B2 | 7/2018 | Brown et al. | |
| 10,052,257 B2 | 8/2018 | Nageshwar | |
| 10,058,478 B2 | 8/2018 | Schnetz et al. | |
| 10,086,199 B2 | 10/2018 | Robertson | |
| 10,130,275 B2 | 11/2018 | Nageshwar | |
| 10,413,719 B2* | 9/2019 | Brown | A61N 1/0529 |
| 11,331,473 B2* | 5/2022 | Brown | A61N 1/36071 |
| 11,813,448 B2* | 11/2023 | Brown | A61N 1/0529 |
| 2003/0050470 A1 | 3/2003 | An et al. | |
| 2003/0149451 A1 | 8/2003 | Chomenky et al. | |
| 2004/0044390 A1 | 3/2004 | Szeles | |
| 2006/0122675 A1 | 6/2006 | Libbus et al. | |
| 2007/0198063 A1 | 8/2007 | Hunter et al. | |
| 2008/0051852 A1* | 2/2008 | Dietrich | A61H 39/002 607/45 |
| 2008/0146549 A1 | 6/2008 | Coleman | |
| 2008/0249439 A1 | 10/2008 | Tracey et al. | |
| 2010/0004715 A1 | 1/2010 | Fahey | |
| 2010/0113965 A1 | 5/2010 | Kanevsky et al. | |
| 2010/0168822 A1 | 7/2010 | Szeles | |
| 2010/0262205 A1 | 10/2010 | De Ridder | |
| 2011/0093033 A1* | 4/2011 | Nekhendzy | A61N 1/36021 607/46 |
| 2011/0160811 A1 | 6/2011 | Walker | |
| 2011/0190569 A1 | 8/2011 | Simon et al. | |
| 2012/0203301 A1* | 8/2012 | Cameron | A61N 1/361 607/45 |
| 2012/0226333 A1 | 9/2012 | Szeles | |
| 2013/0150923 A1 | 6/2013 | Schnetz et al. | |
| 2014/0081368 A1 | 3/2014 | Szeles | |
| 2014/0222114 A1* | 8/2014 | Craig | A61B 5/0205 607/62 |
| 2014/0370476 A1 | 12/2014 | Nageshwar | |
| 2014/0371608 A1 | 12/2014 | Nageshwar | |
| 2014/0371621 A1 | 12/2014 | Nageshwar | |
| 2015/0112405 A1* | 4/2015 | Brown | A61N 1/0502 607/46 |
| 2015/0265830 A1 | 9/2015 | Simon et al. | |
| 2016/0074663 A1 | 3/2016 | De Ridder | |
| 2016/0113526 A1 | 4/2016 | Nageshwar et al. | |
| 2016/0144175 A1 | 5/2016 | Simon et al. | |
| 2017/0143247 A1 | 5/2017 | Nageshwar | |
| 2018/0064603 A1 | 3/2018 | Brown et al. | |
| 2018/0200522 A1 | 7/2018 | Taca, Jr. | |
| 2018/0296435 A1 | 10/2018 | Brown et al. | |
| 2019/0262229 A1 | 8/2019 | Brown et al. | |
| 2022/0072311 A1 | 3/2022 | Taca, Jr. | |
| 2022/0241585 A1 | 8/2022 | Brown et al. | |

FOREIGN PATENT DOCUMENTS

| | | |
|---|---|---|
| WO | 2005001706 A1 | 1/2005 |
| WO | 2014200488 A1 | 12/2014 |
| WO | 2014200489 A2 | 12/2014 |
| WO | 2014200492 A1 | 12/2014 |
| WO | 2014207512 A1 | 12/2014 |
| WO | 2017/044967 A1 | 3/2017 |

OTHER PUBLICATIONS

Response and Terminal Disclaimer filed Apr. 10, 2018 to Non-Final Action dated Mar. 19, 2018 in U.S. Appl. No. 10/010,479 issued Jul. 3, 2018.

Non-Final Office Action dated Aug. 2, 2017 filed in U.S. Pat. No. 9,839,577 issued Dec. 12, 2017.

Response and Terminal Disclaimer filed Sep. 7, 2017 to Non-Final Office Action dated Aug. 2, 2017 in U.S. Pat. No. 9,839,577 issued Dec. 12, 2017.

Non-Final Office Action dated Jul. 15, 2015 filed in U.S. Pat. No. 9,662,269 issued May 30, 2017.

Response filed Nov. 16, 2015 to Non-Final Office Action dates Jul. 15, 2015 in U.S. Pat. No. 9,662,269 issued May 30, 2017.

Final Office Action dated Feb. 25, 2016 filed in U.S. Pat. No. 9,662,269 issued May 30, 2017.

Response and Request for Continued Examination filed on Jun. 27, 2016 to Final Office Action dale Feb. 25, 2016 in U.S. Pat. No. 9,662,269 issued May 30, 2017.

Non-Final Office Action dated Jul. 28, 2016 filed in U.S. Pat. No. 9,662,269 issued May 30, 2017.

Response filed Aug. 25, 2016 to Non-Final Office Action dated Jul. 28, 2016 filed in U.S. Pat. No. 9,662,269 issued May 30, 2017.

Non-Final Office Action dated Dec. 1, 2016 filed in U.S. Pat. No. 9,662,269 issued May 30, 2017.

Response filed Feb. 27, 2017 to Non-Final Office Action dated Dec. 1, 2016 filed in U.S. Pat. No. 9,662,269 issued May 30, 2017.

Roberts, Arthur and Christopher R. Brown. "Percutaneous Peri-Auricular Peripheral Nerve Field Stimulation: A Novel, Non-Opioid Therapy for Diabetic Neuropathy." The Pain Practitioner, vol. 25, 3 (2015): 41-47.

Miranda, Adrian, and Arturo Taca. "Neuromodulation with percutaneous electrical nerve field stimulation is associated with reduction in signs and symptoms of opioid withdrawal: a multisite, retrospective assessment." The American journal of drug and alcohol abuse vol. 44,1 (2018): 56-63. doi:10.1080/00952990.2017.1295459.

* cited by examiner

METHODS OF TREATING DISEASE USING AURICULAR PERIPHERAL NERVE FIELD STIMULATION

CROSS REFERENCE TO RELATED APPLICATIONS

This application is a continuation application of U.S. application Ser. No. 17/725,761, filed Apr. 21, 2022, which is a continuation of U.S. application Ser. No. 16/534,159, filed on Aug. 7, 2019, now U.S. Pat. No. 11,331,473, issued May 17, 2022, which is a continuation application of U.S. application Ser. No. 15/488,416, filed on Apr. 14, 2017, now U.S. Pat. No. 10,413,719, issued Sep. 17, 2019, which claims the benefit of priority under 35 U.S.C. § 119 (e) to U.S. Provisional Patent Application Ser. No. 62/323,369, filed Apr. 15, 2016, and U.S. Provisional Application Ser. No. 62/324,598, filed Apr. 19, 2016, each of which is incorporated herein by reference in its entirety.

FIELD OF THE INVENTION

The invention described herein pertains to devices and methods for treatment of disease by nerve stimulation. More particularly, the present disclosure is related to treating disease including but not limited to pain and drug withdrawal by implanting a device in the peri-auricular area to stimulate cranial nerves.

BACKGROUND

Drug Withdrawal Opioid addiction is a serious public health issue that negatively impacts many communities around the world. There are millions of people who misuse opioids worldwide. In 2013, it was estimated that in the United States, approximately 1.9 million people suffered from substance use disorders related to prescription opioid pain relievers and approximately 517,000 were addicted to heroin. Currently, most individuals with an opioid use disorder are not able to get treatment.

Abrupt discontinuation of heroin or an opioid receptor agonist for the purpose of transitioning to an opioid antagonist, such as naltrexone, requires an "induction phase" including medical supervision to control symptoms. Areas of the brain and brainstem which are normally responsible for homeostasis are typically suppressed by opiates altering both function and the ability to adapt. After removal of the opiates these areas may respond by becoming hyperactive before returning to homeostasis. Certain treatment options, such as antagonists, cannot be prescribed until patients have successfully completed medically supervised withdrawal due to the risk of inducing a precipitated withdrawal. For example, naltrexone completely blocks opiate receptors but cannot be used until the patient is opiate free for several days or a precipitated withdrawal may occur. Extended release forms of naltrexone, which may be effective for the prevention of relapse into opioid dependence, may require seven days or more of a detox process to avoid precipitated withdrawal. Another common complication is the return to opiate use after withdrawal leading to overdose deaths.

Pharmacotherapy has been the main method for the induction phase of treatment of opioid withdrawal. There are challenges to medication-assisted treatment for acute opiate withdrawal and opiate addiction. Some medications for treatment of opiate detox are themselves addicting. For example, methadone and buprenorphine are partial opiate receptor agonists that stimulate opiate receptors. Non-narcotic medications, such as clonidine, anti-spasmodics, and sleeping aids, have unpredictable efficacy. Naloxone, which is an antidote to heroin or opiate overdose, can be life-saving, but has a short half-life and does not provide an efficacious treatment for long-term sobriety.

Patients are more likely to leave treatment early when withdrawal symptoms are not appropriately managed. Pain associated with withdrawal is often a major reason for opting out of treatment. Symptoms of withdrawal may include, but are not limited to, abdominal cramping, diarrhea, cold and hot sweats, dilated pupils, cutis anserine, nausea, vomiting, dehydration, electrolyte disturbances, heart arrhythmias, and aspiration of stomach contents into the lungs leading to lung infections.

Thus, there is a need in the art for methods of treating opioid withdrawal during the period between cessation at least up until administration of a drug such as a pharmaceutical opiate receptor blocking drug. Moreover, there is a need to find an effective, non-pharmacological approach to treat opioid withdrawal, which could remove some of the barriers associated with pharmacotherapy.

Pain Relief

Additionally, analgesia has traditionally been achieved through medication. For example, acute and chronic pain conditions have been treated with opioid or opioid derivative medications. These medications however, are associated with adverse side effects that limit their use. Accordingly there is also a need for new treatment methods to provide relief of pain and discomfort.

Functional Abdominal Pain Disorders

Functional abdominal pain disorders (FAPDs) are a group of functional gastrointestinal disorders with pain as the driving symptom. Examples of FAPDs include irritable bowel syndrome (IBS), functional dyspepsia, functional abdominal pain-not otherwise specified (FAP-NOS) and abdominal migraine. Patients with irritable bowel syndrome (IBS) suffer from chronic abdominal pain despite having no structural or anatomical lesions. Most pharmacological agents used to treat IBS are no better or have minimal gain over placebo. Their complex nature and unclear pathophysiology may make the management of FAPDs challenging. Accordingly there is also a need for new treatment methods to provide relief of FAPDs.

Throughout this disclosure, various publications, patents and patent applications are referenced. The disclosures of these publications, patents and applications in their entireties are hereby incorporated by reference into this disclosure.

SUMMARY OF THE INVENTION

Figure 1:
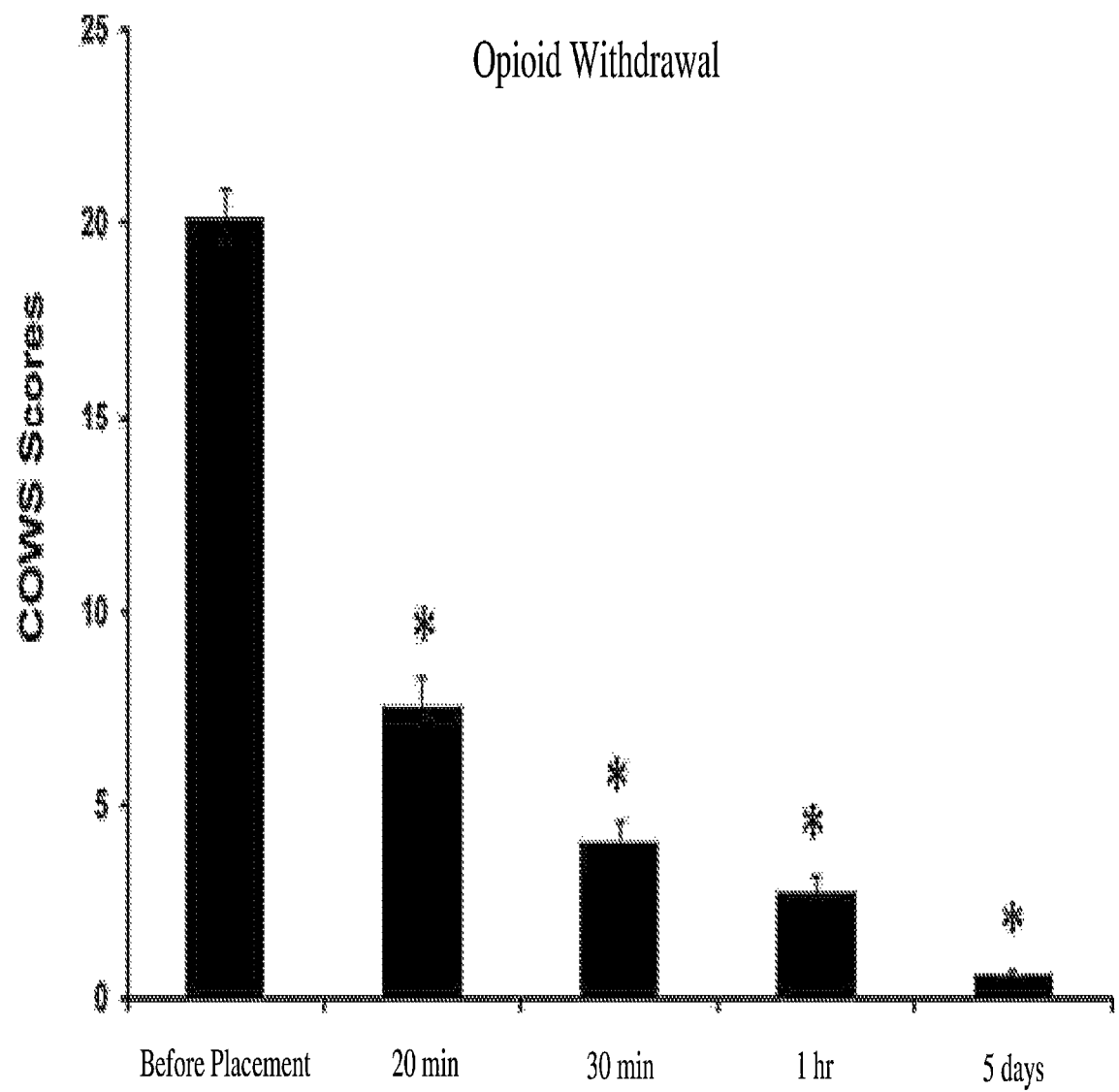
FIG. 1 is a graph showing patients' COWS scores over time before and during treatment with the Bridge.

In some embodiments, the present disclosure provides a method for treating pain and/or discomfort in a patient in need of such treatment. The method comprises stimulating a cranial nerve with an electric signal. For example, the may comprise administering to the patient a stimulator device that provides the electric signal. The device may be any device configured to electrically stimulate nerves near the patient's auricular area. The stimulating step can be administered prophylactically, or can be administered after the onset of the symptoms.

The methods described herein may be used for various therapeutic applications. In some embodiments the methods are used to treat pain by providing analgesia. In further embodiments the methods are used to treat drug addition. A stimulator device may mitigate withdrawal symptoms upon application to a patient. For example, the withdrawal symptoms may be associated with opioids withdrawal. In still further embodiments, the methods are used to treat the symptoms associated with a functional abdominal pain disorder.

In accordance with some embodiments, the method comprises a first step of stimulating a patient's cranial nerve soon after cessation of drug or alcohol use. The stimulation step may occur for several days. The methods described herein may further comprise administering one or more secondary drugs during or after the stimulating step.

Several embodiments of the invention are described by the following enumerated clauses:

1. A method for treating pain or discomfort in a patient comprising stimulating a cranial nerve with an electrical signal.
2. The method of clause 1, wherein the pain or discomfort is a withdrawal symptom.
3. The method of clause 1, wherein the pain or discomfort is a functional abdominal pain disorder.
4. The method of clause 3, wherein the functional abdominal pain disorder is irritable bowel syndrome.
5. The method of any of the preceding clauses, wherein the cranial nerve is in an auricular area of the patient.
6. The method of any of the preceding clauses, wherein the cranial nerve is in a peri-auricular area of the patient.
7. The method of any of the preceding clauses, wherein stimulating the cranial nerve comprises contacting the auricular area of the patient with the electrical signal.
8. The method of any of the preceding clauses, wherein stimulating the cranial nerve comprises contacting the peri-auricular area of the patient with the electrical signal.
9. The method of any of the preceding clauses, wherein the cranial nerve is selected from the group consisting of cranial nerve V, cranial nerve VII, cranial nerve IX, cranial nerve X, and branches of greater and lesser occipital nerves thereof and their associated neurovascular bundles.
10. The method any of the preceding clauses, wherein the cranial nerve is selected from the group consisting of cranial nerve V, cranial nerve VII, cranial nerve IX, and cranial nerve X.
11. The method of any of clauses 2 and 5 to 10, wherein the withdrawal symptom results from cessation of an addictive drug or alcohol.
12. The method of any of clauses 2 and 5 to 11, wherein the withdrawal symptom results from cessation of an addictive drug.
13. The method of clause 11 or 12, wherein the patient abstains from using the addictive drug during the stimulating step.
14. The method of any of clauses 11 to 13, wherein the addictive drug is selected from the group consisting of an opioid, cocaine or a base or salt thereof, nicotine, an amphetamine or substituted amphetamine, a barbiturate, alcohol, a benzodiazepine, or buprenorphine.
15. The method of any of clauses 11 to 14, wherein the addictive drug is an opioid.
16. The method of clause 15, wherein the opioid is selected from the group consisting of morphine, codeine, heroin, hydrocodone, oxycodone, buprenorphine, methadone, nicomorphine, dipropanoylmorphine, desomorphine, acetylpropionylmorphine, dibenzoylmorphine, diacetyldihydromorphine, paramorphine, fentanyl, pethidine, levorphanol, tramadol, tapentadol, dextropropoxyphene, hydromorphone, oxymorphone, ethylmorphine, buprenorphine, and salts thereof.
17. The method of clause 15 or 16, wherein the opioid is selected from the group consisting of heroin, hydrocodone, oxycodone, morphine, fentanyl, and codeine.
18. The method of any of clauses 2 and 5 to 17, wherein the withdrawal symptoms comprise conditions selected from the group consisting of abdominal cramping, diarrhea, cold sweats, hot sweats, dilated pupils, cutis anserine, nausea, vomiting, increased heart rate, restlessness, somatic pain, runny nose, gastrointestinal symptoms, tremors, yawning, anxiety, irritability, fear, and combinations thereof.
19. The method of any of the preceding clauses, further comprising administering a secondary drug to the patient.
20. The method of clause 19, wherein the secondary drug treats one or more of the withdrawal symptoms and addiction.
21. The method of clause 19 or 20, wherein the secondary drug is administered about one day to about two weeks after initiating the stimulating step.
22. The method of any of clauses 19 to 21, wherein the secondary drug is administered about one day to about one week after initiating the stimulating step.
23. The method of any of clauses 19 to 22, wherein the secondary drug is an opioid receptor antagonist.
24. The method of any of clauses 19 to 23, wherein the secondary drug is selected from the group consisting of naloxone, naltrexone, and nalmefene.
25. The method of any of clauses 19 to 24, wherein the secondary drug is naltrexone.
26. The method of any of the preceding clauses, further comprising using transillumination to locate auricular neurovascular bundles of the patient.
27. The method of any of the preceding clauses, wherein the stimulating step occurs for about ten minutes to about one week.
28. The method of any of the preceding clauses, wherein the patient experiences a reduction in the pain or discomfort within one day.
29. The method of any of clauses 2 and 5 to 28, wherein the patient experiences a reduction in the withdrawal symptoms within one day.
30. The method of any of clauses 2 and 5 to 29, wherein the patient experiences a reduction in the withdrawal symptoms within one hour.
31. The method of any of the preceding clauses, wherein the stimulating step comprises administering electrical stimulation pulses to the auricular area of the patient.
32. The method of clause 31, wherein the electrical simulation pulses have a voltage output of about 1V to about 5V.
33. The method of clause 31 or 32, wherein the electrical simulation pulses have a repetition frequency of about 0.5 Hz to about 100 Hz.

34. The method of any of clauses 31 to 33, wherein the electrical simulation pulses have a repetition frequency of about 1 Hz to about 10 Hz.
35. The method of any of clauses 31 to 34, wherein the electrical simulation pulses have a duty cycle of about 10% to about 90%.
36. The method of any of clauses 31 to 35, wherein the electrical simulation pulses have a duty cycle of about 40% to about 60%.
37. The method of any of clauses 31 to 36, wherein the stimulation pulses are generated at a constant current amplitude.
38. The method of any of the preceding clauses, wherein the stimulating step comprises attaching a stimulator device to the auricular area of the patient.
39. The method of any of the preceding clauses, wherein the stimulating step comprises attaching a stimulator device to the peri-auricular area of the patient.
40. The method of clause 38 or 39, wherein the stimulator device is attached percutaneously or transcutaneously.
41. The method of any of clauses 38 to 40, wherein the stimulator device comprises
    (i) a generator for generating electrical stimulation pulses with defined stimulation parameters, (ii) a voltage supply for supplying the generator with electrical energy and (iii) a control device for generating stimulation pulses from the generator having a defined current voltage or current amplitude, a defined duration, a defined repetition frequency and a defined duty cycle and
    at least one therapy electrode connected to the stimulator for providing stimulation pulses to the auricular area.
42. The method of any of clauses 38 to 41, wherein the device is implanted within 2 mm the cranial nerve.
43. The method of any of the preceding clauses, wherein the stimulating step alters response characteristics of amygdala neurons.
44. The method of any of the preceding clauses, wherein the stimulating step alters response characteristics of lumbar spinal neurons.

DETAILED DESCRIPTION OF THE INVENTION

In accordance with Applicants' invention described herein, the embodiments of the numbered clauses provided in the summary above, or any combination thereof, are contemplated for combination with any of the embodiments described in the Detailed Description section of this patent application.

Definitions

In describing and claiming the invention, the following terminology will be used in accordance with the definitions set forth below.

The term "about" as used herein means greater or lesser than the value or range of values stated by 10 percent, but is not intended to designate any value or range of values to only this broader definition. Each value or range of values preceded by the term "about" is also intended to encompass the embodiment of the stated absolute value or range of values.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

As used herein the term "pharmaceutically acceptable salt" refers to salts of compounds that retain the biological activity of the parent compound.

As used herein a "effective" conditions refers to nontoxic but sufficient conditions to provide the desired effect. For example, one desired effect would be preventing the onset of withdrawal symptoms, or reducing the severity, frequency, or duration, of such symptoms. Conditions constituting "effective" will vary from subject to subject, depending on the age and general condition of the individual, mode of administration, and the like.

In accordance with the invention, "clinical benefit" means a response of a patient to treatment with a stimulating method described herein where the response includes overall reduction or pain and/or discomfort, potentially among other clinical benefits.

In accordance with the invention, the term "administering" as used herein includes all means of introducing the stimulating methods and devices described herein to the patient.

Electrical Nerve Field Stimulation

Percutaneous Electrical Neuro-modulating Field Stimulation (PENFS) is a non-narcotic treatment that may be used for conditions such as acute post-surgical and chronic pain conditions, thereby reducing the long-term side effects, dependency, and opiate abuse associated with more traditional pharmacological protocols. PENFS also may be used to mitigate opioid withdrawals. PENFS may also be used for headache control, and other types of pain, including pre and post surgical pain and acute and chronic pain. Although this disclosure refers to Percutaneous Electrical Neuro-modulating Field Stimulation, methods of implementation beyond percutaneous implementation, such as transcutaneous implementation are within the scope of PENFS.

In some embodiments, devices capable of accomplishing PENFS are percutaneously or transcutaneously implanted into the peri-auricular area of a patient, targeting cranial nerves V, VII, IX and X; and branches of the greater and lesser occipital nerves and their associated neurovascular bundles. The external ear contains branches of these nerves, which project to the nucleus tractus solitarius (NTS) and communicate with other brain structures involved in autonomic control and pain such as the amygdala. The dorsal and ventral aspects of the auricle are heavily vascularized from branches of the superficial temporal artery (STA) and the posterior auricular artery (PAA). Cranial Nerves V, VII, IX, X; as well as branches of the greater and lesser occipital nerves are also present in a predicable anatomical fashion. Thus, in some embodiments, the method comprises a clinician to targeting specific cranial neurovascular bundles.

The methods described herein may comprise stimulated sources of extrinsic perivascular innervation, such as those that carry sensory, sympathetic, and parasympathetic nerves. A neurovascular unit includes the functional unit of the endothelial cells, perivascular nerves, and astrocytes. These nerves have different origins and neurotransmitters that can be extrinsic or intrinsic. The external auricle is includes all three embryological tissues that can have influences on the autonomic nervous system. In particular, the trigeminal nerve, vagus nerve, and cervical plexus innervate different areas of the ear. The methods described herein may comprise stimulating one or more of the trigeminal nerve, the vagus nerve, and the cervical plexus.

The theauriculotemporal branch of the trigeminal nerve (CN V) supplies the anterior upper part of the helix consisting mostly of mesodermal tissue. This nerve runs with the superficial temporal artery that supplies the ear. The vagus nerve (CN X) innervates the auricular concha which consists mostly of endodermal tissue. The auricular branch of the vagus nerve passes into the jugular fossa and enters the superior vagal ganglion where their nerve cell bodies are located. Finally, the lesser occipital nerve (C3) innervates the posterior part of the helix and the great auricular nerve (C2, C3) innervates the auricular lobule both of which are mostly ectodermal in embryological origin.

The extended amygdala has been shown to play a role in not only fear conditioning and pain processing, but also in processing the negative emotional state of withdrawal. The methods and devices described herein may be utilized to treat these symptoms. For example, in some embodiments, the devices and methods described herein may show a reduction in the baseline firing of neurons in the central nucleus of the amygdala and a decrease in response to somatic stimulation. In some embodiments, the methods and devices described herein result in neuromodulation of limbic structures that could help alleviate symptoms of withdrawal and offer a noninvasive, drug free alternative.

The apparatuses and methods disclosed herein may reduce sympathetic activity and increase parasympathetic activity by electrical stimulation of the associated cranial nerve bundles via percutaneous implantation of needle arrays into the dermis of the peri-auricular region. Without intending to be bound by theory, it is believed that the methods and devices describes herein activate the nucleus tractus solitarious (NTS), the hypothalamus, the amygdala, and the rostral ventromedial medulla (RVM), affecting both sympathetic and parasympathetic feedback loops into the gray matter of the dorsal horn of the spinal column. As such, the methods and devices described herein may result in disruption of ascending nociceptive stimuli and blocking of descending signals releasing endogenous endorphins and other cytokines often associated with hyperactivity of the previously mentioned entities during opiate withdrawal.

In some embodiments, the methods disclosed herein may alleviate or reduce one or more withdrawal symptoms. Without intending to be bound by theory, the noradrenergic system may be involved in the expression of the somatic symptoms during opiate withdrawal indicating changes in brain noradrenaline and metabolite levels during opiate dependence. The sympathetic nervous system becomes hyperactive and the hypothalamus, the pituitary gland, and the locus coeruleus begin working at above normal levels increasing activity of the peripheral sympathetic nervous system (SNS) during opiate withdrawal, as measured by increases in plasma levels of norepinephrine. Compensatory dysregulation of the sympathetic nervous system co-joined with the hypothalamic-pituitary-adrenal axis, the periaqueductal gray (PAG) area, the amygdala, the ventral tegmental area, nucleus accumbens, and spinal cord lead to an excess of bodily functions normally inhibited by opiates which often include miosis. Mouths may overly dry, mydriasis may occur, dry skin may begin to perspire, dry noses may begin to run, and insensitivity to temperature may develop quickly into hot/cold flashes and chills and precipitation of the physical motor components of opiate withdrawal.

These fluctuations also contribute to excess cortisol release, emotional vulnerability, an inability to fall asleep, anxiety, agitation, panic attacks, increased heart rate, increased blood pressure, muscle tension, tremors, restlessness (akathisia), involuntary movements of the limbs, nausea, vomiting, and stomach discomfort. Other commonly observed symptoms including diarrhea and lacrimation may depend on peripheral opiate receptors. By applying the methods of the present disclosure such symptoms may be alleviated or reduced.

In the peripheral nervous system (PNS), beta-endorphins produce analgesia by binding to opioid receptors at pre- and post-synaptic nerve terminals, primarily exerting their effect via presynaptic binding. When bound, a cascade of interactions results in inhibition of the release of tachykinins, particularly substance P, a key protein involved in the transmission of pain contributing to allodynia and hyperalgesia commonly experienced during opiate withdrawal. As stated above, the methods of the present may alleviate or reduce one or more of these symptoms.

Additionally, persistent irritation of the microglia distorts the feedback patterns of the neuromatrix with subsequent endocrine, immune, and autonomic nervous system changes; and impairs descending medullary inhibition. Without intending to be bound by theory, it is believed that the methods and devices described herein reduce this irritation and the associated microglial inflammation.

In one embodiment, the methods and devices described herein can be used for both human clinical medicine and veterinary applications. Thus, a "patient" can be administered a method herein, and can be human or, in the case of veterinary applications, can be a laboratory, agricultural, domestic, or wild animal. In one aspect, the patient can be a human, a laboratory animal such as a rodent (e.g., mice, rats, hamsters, etc.), a rabbit, a monkey, a chimpanzee, domestic animals such as dogs, cats, and rabbits, agricultural animals such as cows, horses, pigs, sheep, goats, and wild animals in captivity such as bears, pandas, lions, tigers, leopards, elephants, zebras, giraffes, gorillas, dolphins, and whales.

In reference to opioid withdrawal, the Clinical Opiate Withdrawal Scale (COWS) scoring system may be used to evaluate alleviation of a patient's symptoms. In some embodiments, withdrawal symptoms are reduced within about 5 minutes, about 15 minutes, about 20 minutes, about 30 minutes, about 60 minutes, about 2 hours, about 3 hours, or about 6 hours. For example, a patient's COWS scores may be reduced by greater than about 25%, greater than about 50%, or greater than about 60% within 20 minutes after initiation of nerval stimulation. In some embodiments, a patient's COWS scores may be reduced by greater than about 50%, greater than about 75%, or greater than about 80% within 60 minutes after initiation of nerval stimulation.

Advantageously, the methods and devices disclosed herein constitute an effective, non-pharmacological approach that may 1) entail minimal clinician training, 2) be readily available to physicians and advanced care providers, 3) have minimal to no side-effects, and 4) remove the fear of inducing a precipitated withdrawal would be critical in improving and expanding treatment for opioid addiction. In some embodiments, the methods and devices described herein can be used by physician extenders without limitations on the number of subjects treated. In general, the methods and devices described herein offer rapid and effective improvement could lead to improved compliance and better treatment outcomes.

Electrical Nerve Field Stimulation Devices

The nerve may be stimulated by a stimulator device including a generator for generating electrical stimulation pulses with defined stimulation parameters. The stimulator may comprise at least one needle electrode array for insertion into the skin surface of an area to be stimulated. Also, the stimulator device may comprise a power supply for supplying the generator with electrical energy.

One example of device included in the present disclosure are those described in U.S. Patent Pub. No. 2015/0112405, incorporated by reference herein in its entirety.

Another example of group of percutaneously implanted devices of the present disclosure is the Neuro-Stem System (NSS), Innovative Health Solutions, INC, Versailles, Indiana. The NSS collectively refers to devices including the Bridge devices, Innovative Health Solutions, INC, Versailles, Indiana, the Electro Accupuncture Device (EAD), Innovative Health Solutions, INC, Versailles, Indiana, and the Military Field Stimulator (MFS), Innovative Health Solutions, INC, Versailles, Indiana. The devices may be safe, fast-acting, and effective in pain relief and reduction in pain medication consumption.

More particularly, the NSS may be a group of neurostimulation medical devices each comprising a battery operated solid state generator externally affixed to the skin behind a patient's ear, four wire connecting leads, and four attached electrode/needle arrays each including four 1.5 mm needles designed to be percutaneously implanted into the dermis of the patient's external ear.

In one embodiment, the auricular peripheral nerve stimulators of the present disclosure are a battery-operated, single-use devices that have a preprogrammed frequency, pulse, and duration for the stimulation of selected cranial and/or peripheral nerves and corresponding neural vascular bundles of auricular and periauricular areas. In one embodiment, the device power supply connects via three or more electrical conduit wires, sheathed in electrically insulating material, to one or more therapy electrode arrays comprised of multiple needles each and one reference electrode.

In another embodiment, the device comprises two or more needle arrays comprised of multiple needles each. In another embodiment, the device comprises three or more needle arrays comprised of multiple needles each. In another embodiment, the device comprises four or more needle arrays comprised of multiple needles each. In another embodiment, the needle arrays are comprised of two or more needles each. In another embodiment, the needle arrays are comprised of three or more needles each. In another embodiment, the needle arrays are comprised of four or more needles each. In another embodiment, the needle arrays are comprised of five or more needles each. In another embodiment, the needle arrays are comprised of six or more needles each.

The stimulation devices of the present disclosure may include a generator for generating stimulation pulses with defined stimulation parameters, such a defined voltage or a defined current, a defined duration, a defined repetition frequency and a defined duty cycle.

The electrical stimulation device electrical stimulation pulses may have a repetition frequency of about 0.5 to about 100 Hz, about 0.5 to about 50 Hz, about 0.5 to about 25 Hz, about 0.5 to about 10 Hz, about 1 to about 100 Hz, about 1 to about 50 Hz, about 1 to about 25 Hz, or about 1 to about 10 Hz. Also, the electrical stimulation device electrical stimulation pulses may have a duty cycle of about 10 to about 90%, about 10 to about 70%, about 20 to about 90%, about 20 to about 70%, about 30 to about 90%, about 30 to about 70%, or about 40 to about 60%. In some embodiments, the stimulation pulses are generated at a constant current amplitude.

In some embodiments, the stimulation conditions may be adjusted based on a patient's muscle activity, parameters corresponding to breathing, or parameters corresponding to cerebral activity, such as electrical activity of neural cells including brain cells, or electrical activity recorded from the ear or any other suitable point on the body of a human being. Other sensors may be applied as well, like a sensor to measure body temperature, a sensor to measure pressure, and a sound sensor, like a microphone.

In some embodiments, each therapy electrode has two or more needle electrodes, which in an exemplary embodiment is four (4) in number. In one embodiment, the number of therapy electrodes is selected from the group consisting of 2, 3, 4, 5, 6, 7, 8, 9, 10, or more. In another embodiment, the number of needle electrodes per therapy electrode is selected from the group consisting of 2, 3, 4, 5, 6, 7, 8, 9, 10, or more. In one embodiment, the number of needle electrodes per therapy electrode is 2-10. In one embodiment, the number of needle electrodes per therapy electrode is 3-9. In one embodiment, the number of needle electrodes per therapy electrode is 4-8.

Each reference electrode includes at least at least one needle electrode. The therapy electrodes and reference electrode are inserted into the skin surface in the area to be stimulated. The reference electrode provides a ground connection for electronic circuit located within the stimulator.

The devices of the present disclosure provide an apparatus for stimulating auricular points on the human ear is provided using low voltage pulses that are generated and delivered by portions of the apparatus, particularly by percutaneously implanted needle electrodes into the cranial and/or peripheral nerves and corresponding neural vascular bundles of the auricular and periauricular areas.

In order to attach the devices described herein to a patient's skin surface, a fastening element, such as an adhesive element, may be provided. Besides the adhesive element, other fastening methods, e.g. via magnets, elastic bands or the like can be used.

In another embodiment, the devices described herein are single use devices that are physician applied for ambulatory, continuous, home based therapy. These devices may be percutaneously implanted into the cranial and/or peripheral nerves and corresponding neural vascular bundles of the auricular and periauricular areas as ascertained by the disclosed method of evaluating and implanting of the electrode/needle array. This includes transillumination of the auricular and periauricular tissues and surrounding neurovascular anatomy. The auricular peripheral nerve stimulator system allows for continuous, intermittent neural stimulation for about 1 day, about 2 days, about 3 days, about for days, or about 5 days.

In another embodiment, the devices are ambulatory, physician applied, minimally invasive applications of electrical neural stimulation implanted directed into the neurovascular bundles of the external ear verified by transillumination co-joined with skin impedance measurement. In another embodiment, a generator located behind the ear, produces electrical stimulation impulses, which are transferred via an electrode/needle array to branches of cranial and/or occipital nerves and sympathetic fibers of the arterial branches.

In another embodiment, electrode/needle array implantation into the skin of the ear allows for direct access to branches of cranial nerves V, VII, IX, and X as well as branches of the occipital nerves. Direct access to the arterial branches of the head and neck are accessible and reduction of sympathetic stimulation results in an increase of vascular flow rate, reduction of vascular resistance and increase of perfusion. The arterial branches of the superficial temporal artery and the posterior auricular artery form a rich interconnecting complex network the terminal branches of which anastomose throughout the ear.

In another embodiment, the auricular peripheral nerve stimulator alters production and utilization of serotonin via vagal stimulation, and meningovascular dilation secondary to decreased sympathetic (or increased parasympathetic) tone.

In some embodiments, the devices described herein are provided in disposable convenience kits comprising one or more of a generator, sterile wire leads with arrays attached, transilluminator, tweezers, surgical marking pen, several adhesives, bandages, disinfectant, and IFU (instructions for use).

Methods of Electrical Nerve Field Stimulation

The methods described herein may comprise using a stimulator device. The device may be physician applied for ambulatory, continuous, home based therapy. In one embodiment, a stimulator is percutaneously implanted into the cranial and/or peripheral nerves and corresponding neural vascular bundles of the auricular and periauricular areas as ascertained by the method of evaluating and implanting of the electrode/needle array provided in the present invention. This includes transillumination of the auricular and periauricular tissues and surrounding neurovascular anatomy. The auricular peripheral nerve stimulator system allows for continuous, intermittent neural stimulation.

First, the chosen external ear may be cleaned with an astringent to remove any surface oils or debris. Furthermore, the subject's external ear and the generator location may be disinfected by alcohol pads.

Next, the patient's ear is transilluminated to identify neurovascular bundles that are to be avoided during needle implantation. More particularly, methods described herein may include transillumination of the auricular and periauricular tissues and surrounding neurovascular anatomy depending upon the symptoms or other conditions of a particular patient. It should be appreciated that one skilled in the art can identify auricular points and/or their correlation with different health. Once such points are identified by a health care professional, the device of this invention is employed to deliver a pulsed voltage to such points.

Visualization may be accomplished due to the thickness of the tissue of the external ear being thin enough that a focused light (transilluminator) can pass through the tissue (transillumination). Also, there is a difference in density between the auricular tissues and the auricular neurovascular bundles allowing the bundles to be visualized and outlined. In other embodiments, both measurement of the rate of arterial blood flow and the vessel anatomy can be visualized and isolated using ultra sonic imaging and other techniques used to directly visualize neurovascular or vascular tissues.

The verification of the cranial nerves, peripheral nerves, arterial branches, and neurovascular bundles may be ascertained by anatomy and visualization. There are anatomical areas (zones), which have predictable and reproducible concentrations of the cranial nerves, peripheral nerves, arterial branches, and neurovascular bundles but no set "points" to learn and follow. The combination of the understanding of anatomy, visualization, and proper percutaneous implantation of the needle/electrode array may determine proper transfer of the electricity into the neurovascular bundles.

Also, as discussed above, the dorsal and ventral aspects of the auricle are heavily vascularized from branches of the superficial temporal artery (STA) and the posterior auricular artery (PAA). Cranial Nerves V, VII, IX, X; as well as branches of the greater and lesser occipital nerves are also present in a predicable anatomical fashion. In some embodiments, this helps the clinician to target specific cranial neurovascular bundles.

In one particular embodiment, a lighted, optic tip of a transillumination device is placed directly against the skin on the ventral or dorsal aspect of the ear at 90 degrees so the concentrated light passes through the tissue. The light can be a direct, focused light or an array of lights of any color spectrum. Since the light passes through the tissue and the auricular tissue has a different density than the neurovascular bundles, this may in essence outline the arterial branches and the neurovascular vascular bundles so they can be seen.

Random percutaneous implantation of the arrays into a heavily vascularized area could result in a high incidence of bleeding. The technique of transillumination avoids random placement and may help reduce the incidence of insertion directly into the peripheral arterial branches, greatly reducing the potential of bleeding. The use of FDA approved bio-compatible materials, sterilization of the arrays and proper skin disinfecting technique, as outlined in the IFU (instructions for use) reduces the incidence of dermatitis, and practically eliminates the chance of infection.

The electrode/needle complex(s) may be implanted to stimulate the nerves including but not limited to the arterial branches, the cranial nerves, peripheral nerves, and the neurovascular bundles. The generator may be attached with adhesive to the skin behind the ear just over the mastoid process. Needles are inserted into the dorsal and ventral aspects of the ear. The needles may be placed within about 1 to about 1.5 mm of the visible arterial branches to create a field effect. In some embodiments, the electrode/needle array connected to the lead wires are percutaneously implanted into the proper anatomical location being sure to penetrate the skin so implantation is percutaneous within about 1 mm or within about 2 mm of the chosen neurovascular bundles. The devices may be implanted using a percutaneous or transcutaneous approach.

There is a natural tissue resistance to electricity. The implanted needle cannot be directly into an arterial branch. Percutaneous implantation of one or more needle/electrode complex(s) or an array beyond the capability of the tissue to transfer the electricity will cause tissue damage and pain with little or no energy transfer to the neurovascular bundles, arterial branches, peripheral or cranial nerves. Percutaneous implantation of a needle or needle/array directly into a main arterial branch will cause pain and bleeding.

In one particular embodiment, the needle/electrode complex(s) is implanted percutaneously within 2 mm of the neurovascular bundles (as visualized) but not directly into an arterial branch by placing the needle into the skin at 90 degrees from either the dorsal or ventral aspect of the ear depending upon which of the cranial nerves, occipital nerves, neurovascular bundles, or arterial branches are to be targeted. The needle should not be inserted directly into a main arterial branch. The needle must pass through the outer dermis to be classified as percutaneous. Placing any type of stimulation to the outer skin without complete skin penetration is considered transcutaneous.

The actual location and determination of needle placement (called points) may be similar to those of the tradition and theory of acupuncture. However, the present invention provides methods not based upon acupuncture technique or "points" but rather peripheral nerve field stimulation, anatomical location of cranial nerves, peripheral nerves, arterial branches and/or neurovascular bundles, and energy transfer based upon accepted laws of energy transfer in human tissue. Therefore, in some embodiments, the method does not require precise placement of needles in specific "acupoints." Peripheral nerve field stimulation considers neuroanatomy, blood vessel anatomy, proximity of the electrodes to the actual nerves being stimulated, and verification of electrode proximity.

The methods described herein vary from auricular acupuncture in several ways. For example, the verification of the bundles may ascertained by physical anatomy and visualization; there are anatomical areas, which have concentrations of the cranial nerves and arterial branches but no set "points" to learn and follow; location of placement of the electrode/needle complex must be individualized and is not "pre set;" and the methods comprise neurovascular stimulation and targeted stimulation of the cranial nerves or peripheral nerves, not acupuncture points (chi, hot/cold, or reflex points).

Verification of correct placement may be determined by patients noting the pulsing of the electricity, and/or enlarging of the associated arteries by unaided visual inspection. In one embodiment, the method further comprises following up with transillumination as described herein to help verify arterial reaction. In another embodiment, the method further comprises measurement of an increase in blood flow, as measured or determined by any method or device.

In some embodiments, upon percutaneous implantation and activation of a generator, a fractal geometric electronic field is produced which is designed to stimulate the targeted neurovascular bundles.

The methods may comprise delivering about 0.5V to about 10V, about 1V to about 7V, about 1V to about 5V, about 2 to about 4V or about 3.2V. The voltage may be delivered with alternating frequencies of stimulation.

The methods described herein may be applied for about 10 minutes, about 15 minutes, about 30 minutes, about 1 hour, about 3 hours, about 6 hours, about 12 hours, about 1 day, about 2 days, about 3 days, about 4 days, about 5 days, up to about 10 minutes, up to about 15 minutes, up to about 30 minutes, up to 1 about hour, up to 3 about hours, up to 6 about hours, up to about 12 hours, up to about 1 day, up to about 2 days, up to about 3 days, up to about 4 days, up to about 5 days, or up to about 7 days. In some embodiments, stimulation is provided for a total of about 120 hours, allowing for physician applied ambulatory treatment of acute pain secondary to opiate withdrawal.

The method may comprise careful monitoring of the patient's vital signs and the availability of immediate supportive care. In some embodiments, a patient is assessed by measuring heart rate, sweating, restlessness, pupil size, somatic pain, runny nose, GI upset, tremors, yawning, anxiety or irritability, gooseflesh skin, or a combination thereof. In some embodiments, due to the stimulation of the peripheral branches of the Vagus nerve, possible vaso-vagal response may be taken into consideration. Patient's pre-existing health conditions such as seizures, bleeding disorders, on-demand electrical implants, medications, and autonomic nervous system status may be taken into consideration.

Depending upon the type of pain or discomfort as described herein, a wide range of permissible conditions for treatment are contemplated herein. The treatment sessions may be single or divided, and may administered according to a wide variety of protocols, including q.d., b.i.d., t.i.d., or even every other day, biweekly (b.i.w.), once a week, once a month, once a quarter, and the like. Further, a staggered regimen, for example, one to five days per week can be used as an alternative to daily treatment, and for the purpose of the methods described herein, such intermittent or staggered daily regimen is considered to be equivalent to every day treatment and is contemplated. In various embodiments of the invention, the methods and devices described herein may be administered more than once and intermittently. By "intermittent administration" is intended administration of effective conditions, followed by a time period of discontinuance, which is then followed by another administration of the effective conditions. Additional treatment sessions may be administered to the patient to prevent the recurrence of withdrawal symptoms.

Any effective regimen for administering the devices and methods described herein can be used. Effective conditions, as herein defined, may be dependent upon many factors, including but not limited to, the type of disease or condition and its severity, i.e., the extend of the patient's pain or discomfort, the patient's general health, size, age, and the nature of the treatment, i.e. short-term or chronic treatment.

As further described herein, the methods of the present disclosure lead to low reported incidences of bleeding, dermatitis, infection, and syncope support these positions. Nevertheless, in some embodiments the methods described herein further comprise monitoring of the patient's vital signs and/or immediate availability of supportive care.

Secondary Drugs

In accordance with one embodiment of the present disclosure, the methods described herein further comprise co-administering one or more secondary drugs. The term "co-administered" as used herein means that the secondary drug may be administered together with the devices and methods of the present disclosure as part of a single treatment step or as separate, multiple steps. For example, the secondary drug can be administered before, after, or in conjunction with the methods and devices of the present disclosure to enhance or supplement their effectiveness in treating pain or discomfort. In accordance with one embodiment the patient is treated with the methods and devices described herein, immediately followed by the secondary drug. Advantageously, when the methods and devices described herein are administered in conjunction with other agents used for treating pain or discomfort, the amount of the active agents needed for efficacy may be reduced relative to when one agent is used alone.

Alternatively, the additional agent may be administered prior to, consecutively with, or following the administration of the bridge agent. The co-administration of a bridge agent and a second therapeutic agent, to a patient does not preclude the separate administration of that same therapeutic agent, any other second therapeutic agent or any compound of this invention to the patient at another time during a course of treatment.

In some embodiments the device is administered during the time period when a patient is susceptible to precipitated withdrawal. For example, the device may be used for about 1 day, about 2 days, about 3 days, about 4 days, or 5 days before administering the secondary drug.

In some embodiments, the methods described herein may further comprise administering a secondary drug for the treatment of withdrawal symptoms. The secondary drug may be an opioid receptor antagonist. For example, secondary drug may be naloxone, naltrexone, or nalmefene.

The aversive and anxiety-like state during withdrawal is thought to involve stress-related systems such as noradrenergic pathways. In some embodiments, the methods described herein further comprise administering one or more drugs that inhibit noradrenergic release such as clonidine.

In some aspects of these embodiments, a parenteral dosage form selected from the group consisting of intradermal, subcutaneous, intramuscular, intraperitoneal, intravenous, and intrathecal may be employed to administer the secondary drug.

In some embodiments the secondary drug is provided as a salt. Suitable acid addition salts are formed from acids which form non-toxic salts. Illustrative examples include the acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base salts of the secondary drug described herein are formed from bases which form non-toxic salts. Illustrative examples include the arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulphate and hemicalcium salts.

In one embodiment, a patient is administered a composition comprising the secondary drug in a standard pharmaceutically acceptable carrier using any of the standard routes of administration known those skilled in the art. The carriers can be excipients. The choice of carrier will to a large extent depend on factors such as the particular mode of administration, the effect of the carrier on solubility and stability, and the nature of the dosage form. Pharmaceutical compositions suitable for the delivery of second compound described herein and methods for their preparation will be readily apparent to those skilled in the art. Such compositions and methods for their preparation may be found, for example, in Remington: The Science & Practice of Pharmacy, 21th Edition (Lippincott Williams & Wilkins, 2005), incorporated herein by reference.

In one illustrative aspect, a pharmaceutically acceptable carrier includes any and all solvents, dispersion media, coatings, antibacterial and antifungal agents, isotonic and absorption delaying agents, and the like, and combinations thereof, that are physiologically compatible. In some embodiments, the carrier is suitable for parenteral administration. Pharmaceutically acceptable carriers include sterile aqueous solutions or dispersions and sterile powders for the extemporaneous preparation of sterile injectable solutions or dispersions. Supplementary active compounds can also be incorporated into compositions of the invention.

The pharmaceutical compositions of the invention include those suitable for oral, rectal, nasal, topical (including buccal and sublingual), vaginal or parenteral (including subcutaneous, intramuscular, intravenous and intradermal) administration. In certain embodiments, the secondary drug is administered transdermally (e.g., using a transdermal patch or iontophoretic techniques). Other formulations may conveniently be presented in unit dosage form, e.g., tablets, sustained release capsules, and in liposomes, and may be prepared by any methods well known in the art of pharmacy.

In certain embodiments, the secondary drug is administered orally. Compositions of the present invention suitable for oral administration may be presented as discrete units such as capsules, sachets, or tablets each containing a predetermined amount of the active ingredient; a powder or granules; a solution or a suspension in an aqueous liquid or a non-aqueous liquid; an oil-in-water liquid emulsion; a water-in-oil liquid emulsion; packed in liposomes; or as a bolus, etc. Soft gelatin capsules can be useful for containing such suspensions, which may beneficially increase the rate of compound absorption.

In one aspect, a secondary drug as described herein may be administered directly into the blood stream, into muscle, or into an internal organ. Suitable routes for such parenteral administration include intravenous, intraarterial, intraperitoneal, intrathecal, epidural, intracerebroventricular, intraurethral, intrasternal, intracranial, intratumoral, intramuscular and subcutaneous delivery. Suitable means for parenteral administration include needle (including microneedle) injectors, needle-free injectors and infusion techniques.

In various embodiments, formulations may be for immediate and/or modified release. In one illustrative aspect, active agents of the secondary drug compound may be administered in a time release formulation, for example in a composition which includes a slow release polymer. The second compound can be prepared with carriers that will protect the second compound Biodegradable, biocompatible polymers can be used, such as ethylene vinyl acetate, polyanhydrides, polyglycolic acid, collagen, polyorthoesters, polylactic acid and polylactic, polyglycolic copolymers (PGLA). Methods for the preparation of such formulations are generally known to those skilled in the art. In another embodiment, the secondary drug described herein may be continuously administered, where appropriate.

In one embodiment a kit is provided for administering the devices and secondary drugs described herein to a patient. The kit comprises a device of the present disclosure, optionally one or more secondary drugs, and optionally means for separately retaining the compositions, such as a container, divided bottle, or divided foil packet. Depending on the route of administration, the kit may include an inhaler if said second composition is an inhalable composition; a syringe and needle if said second composition is an injectable composition; a syringe, spoon, pump, or a vessel with or without volume markings if said composition is an oral liquid composition; or any other measuring or delivery device appropriate to the dosage formulation of the composition present in the kit. In one embodiment the kit is provided with a device for administering the second composition to a patient, e.g. syringe needle, pen device, jet injector or other needle-free injector. In one embodiment the device is a syringe. In some embodiments, the kit includes instructions for use of the bridge and optionally one or more secondary drugs.

Opioid Withdrawal

Some embodiments of the present disclosure relate to treating a patient suffering from withdrawal symptoms. Patients suffering from such symptoms are treated using the methods and devices described herein, in a manner and for a time sufficient to reduce the severity, frequency or duration of their symptoms.

In some embodiments, the methods described herein further comprise administering an opioid receptor antagonist to a patient in need thereof. In illustrative embodiments, the opioid receptor antagonist may be naloxone, naltrexone, or nalmefene, or an extended release formulation thereof. In further embodiments, the opioid receptor antagonist may be naltrexone or an extended release formulation thereof, such as Vivatrol®. The antagonist may be administered to a patient after initiating neuronal stimulation or after completing neuronal stimulation. For example, a patient may be treated using the methods and devices described herein leading up to the time that the patient may be administered an opioid receptor antagonist without risk of precipitated withdrawal.

Advantageously, the methods described herein offer a non-narcotic option to opiate detox and also have the potential for shortening the transition from opioid use to an opioid receptor antagonist, such as Vivitrol®, while mitigating withdrawal symptoms. Such a protocol may have particular utility regarding incarcerated individuals minimizing emergency department treatment and reducing costs secondary to withdrawal symptoms.

Without intending to be bound by theory, the methods described herein may include disrupting ascending nociceptive stimuli and blocking of descending signals releasing endogenous endorphins and other cytokines often associated with hyperactivity of the previously mentioned entities during opiate withdrawal. The physical components commonly associated with opioid withdrawal are a result of the complex interaction of biological feedback loops influenced by the autonomic nervous system. Peri-auricular percutaneous electrical nerve field stimulation the devices described herein is an efficacious way to help reduce symptoms often associated with opioid withdrawal by stimulating areas of the brain via cranial nerves concentrated in the peri-auricular dermis greatly reducing symptoms commonly associated with opioid withdrawal.

In some embodiments, the withdrawal symptom treated by the methods and devices described herein include one or more of abdominal cramping, diarrhea, cold sweats, hot sweats, dilated pupils, cutis anserine, nausea, vomiting, increased heart rate, restlessness, somatic pain, runny nose, gastrointestinal symptoms, tremors, yawning, anxiety, irritability, fear.

Analgesia and Hemodynamics

In some embodiments, stimulating cranial nerves by peri-auricular PENFS may alter intracranial hemodynamics. More particularly, the methods disclosed herein provide a nonpharmaceutical approach to alteration of intracranial hemodynamics to achieve analgesia.

In some embodiments, the methods disclosed herein stimulate the cranial nerves anatomically located in the peri-auricular area directly affecting the extrinsic perivascular innervation, as well as the micro-vascular bed, of the intracranial arteries to decrease flow resistance and increase cerebral perfusion.

Auto-regulation of cerebral blood flow refers to the ability to maintain a relatively constant blood flow despite changes in perfusion pressure. Auto-regulation is particularly well developed in the brain. Chronic pain, inflammation, neuropsychiatric disorders, and stress may alter the autonomic nervous system and bias ANS/CNS auto-regulation through multiple pathways.

Neuromodulation using the methods and devices of the present disclosure alters hemodynamics of cerebral circulation. These devices and methods produce significant changes in cerebral hemodynamics as a result of cranial nerve stimulation.

Neuromodulation utilizing the methods and devices of the present disclosure may be administered as a therapeutic approach for pain conditions. Such treatment may be aimed at reducing the long-term side effects, dependency, and opiate abuse associated with more traditional pharmacological protocols. Stimulation of cranial and cervical nerves described herein may have an effect on the neuromatrix, altering the neuro-modulating feedback loops; resulting in pain reduction. Stimulating these cranial nerves, and their posited effects upon the neuromatrix also may predict altered autonomic modulation of intracranial hemodynamics.

Without intending to be bound by theory, the neuromatrix theory predicts pain perception and response to be moderated by a series of entangled feedback loops, consistent with the maintenance of homeostasis. It further predicts pain-modulating factors outside of the somatic sensory pathways. Several cranial and cervical nerves participate in both the somatic and exo-somatic pathways of the neuromatrix, and thus pain modulation. Among these are CN's V, VII, X, and occipital nerve, the terminal branches of which are represented in the external human auricle.

In some embodiments, hemodynamics may be measured using transcranial Doppler (TCD). As used herein, TCD refers to a noninvasive ultrasound evaluation of the cerebral arteries in real-time. It involves using a low frequency, e.g. 2 MHz or less, transducer on specific bone windows to allow for dynamic monitoring of cerebral blood flow velocity and vascular resistance.

Combined with waveform morphology, indices derived from flow velocity readings including the Gosling's pulsatility index (PI) and the Pourcelot resistivity index (RI) identify increased cerebral vascular resistance and hyper dynamic flow states, which may be used to characterize certain clinical conditions. The TCD ultrasound uses pulsed wave Doppler to image at various depths, and the received echoes generate electrical pulses in the ultrasound transducer that are processed to produce spectral waveforms with peak systolic velocity and end diastolic velocity values.

In some embodiments, the NSS neuromodulation device stimulates the extrinsic perivascular innervation and the micro-vascular bed to decrease flow resistance and increase cerebral perfusion after percutaneous implantation and activation in the peri-auricular region. Peripheral vascular constriction is a result of sympathetic stimulation. Vagal stimulation can reduce sympathetic drive.

In some embodiments, the methods and devices described herein produce a neuro-modulating signal ranging from about 1 to about 10 kQ in intervals of about 100 ms, a bipolar impulse width of about 1 ms with a duty cycle of about 2 hr duty/2 hr rest for a total of about 120 hours.

Amygdala

In some embodiments, neurostimulation with the methods and devices described herein decreases the baseline firing of amygdala neurons and attenuates the response to somatic stimulation. The amygdala, in particular, is a brain region which is involved in pain processing, and activation of this area has also been associated with the emotional component of pain and fear conditioning and the negative emotional state of withdrawal to opioids and drug craving.

Attenuation may occur within about 10 minutes, within about 15 minutes, within about 30 minutes, or within about 1 hour. Without intending to be bound by theory, this attenuation may modulate pain responses in both humans and animals as well as improve in the negative emotional state associated with drug withdrawal.

Lumbar Spinal Neurons

In some embodiments, neurostimulation with the methods and devices described herein may also alter the response characteristics of lumbar spinal cord neurons. More particularly, neurostimulation with the methods and devices described herein may decrease the spontaneous firing and response to somatic stimulation of lumbar spinal neurons. In further embodiments, auricular stimulation as described herein influences the descending modulatory effect on spinal neurons.

Abdominal Pain

In some embodiments, the methods and devices described herein may be used as a non-pharmacological treatment option for patients with chronic abdominal pain, such as functional abdominal pain disorders including but not limited to irritable bowel syndrome (IBS). In some embodiments, the methods described herein result in about 10%, about 20%, about 30%, or about 40% improvement in abdominal pain. Abdominal pain may be measured based on patient reported outcomes (PROs). In some embodiments, auricular neurostimulation as described herein may significantly prevent the development of post-inflammatory visceral and somatic hypersensitivity, such as that associated with TNBS colitis.

Hyperalgesia occurs with IBS and refers to an exaggerated pain response to a normally noxious stimulus. Visceral and somatic hyperalgesis can occur in humans and animals following inflammation in the colon. In some embodiments, a patient develops chronic IBS following a gastrointestinal infection.

The methods and devices described herein include the following examples. The examples further illustrate additional features of the various embodiments of the invention described herein. However, it is to be understood that the examples are illustrative and are not to be construed as limiting other embodiments of the invention described herein. In addition, it is appreciated that other variations of the examples are included in the various embodiments of the invention described herein.

Example 1

This study aimed to determine the effects of the Bridge, Innovative Health Solutions, INC, Versailles, Indiana, on withdrawal scores during the induction phase of opioid withdrawal therapy and the percentage of subjects who successfully transitioned to medication assisted therapy (MAT).

Adult patients (≥18 years old) who met DSM-IV criteria for opioid dependence and voluntarily presented to outpatient drug treatment clinics between June 2015 and July 2016 were included in this retrospective study. Inclusion criteria included a minimum age of 18 years old and a history of dependence on heroin or other opioids such as prescription narcotics, methadone, and buprenorphine/naloxone. A total of 73 subjects were included. In this cohort, the mean age was 32.9 years old and 65% were male. The mean length of drug use was 70 months and 90.5% of the subjects had been using opioids for at least 2 years. 68% of patients had used heroin, 23% had used prescription narcotics, 33% had used buprenorphine/naloxone, and 7% had used methadone. Patients were excluded if they reported a history of dependence on alcohol, pregnancy, or inability to consent to the treatment. A history of benzodiazepines or marijuana use was not a contraindication to Bridge placement. Participating clinics located in St. Louis, MO, Liberty, IN, Florence, KY, Anchorage, AK, Rising Sun, IN, Richmond, IN, Dayton, OH, and Indianapolis, IN provided data from patients treated with the Bridge. The participating treatment centers provided individualized evaluation, stabilization, and treatment with a team of physicians, nurses, counselors, and case managers. Variations exist among the eight outpatient clinics with an approximate daily census ranging from 4 to 25 patients.

Medical records were reviewed for every opioid-dependent individual who was voluntarily treated with the Bridge. Data obtained from all subjects such as demographics and history that included age, gender, approximate length of addiction, and substances used were obtained from chart review. Urine analysis to screen for concomitant use of other substances was performed prior to start of treatment in all patients.

Initial Clinical Opioid Withdrawal Scale (COWS) scores were recorded at baseline and at 20, 30, and 60 minutes in all patients. These scores were extracted from the chart along with scores recorded 5 days after Bridge placement, when available. The scores ranged from 0 to 48 and are rated as mild (5-12), moderate (13-24), moderately severe (25-36), or severe (>36).

Each patient's ear was cleaned with alcohol wipes and transilluminated to identify neurovascular bundles to be avoided during needle implantation. The generator was attached with adhesive to the skin behind the ear just over the mastoid process. There were four leads that came off of the generator, each with sterile 2 mm titanium needles that were inserted into the dorsal and ventral aspects of the ear. The array was place in four general areas within 1-1.5 mm of the visible arterial branches to create a field effect. The Bridge delivered 3.2V with alternating frequencies of stimulation and had a battery life of 5 days.

Patients were observed after Bridge placement, and the majority was sent home after symptoms of withdrawal were relieved, usually after the first hour. The use of any rescue medications during the first hour of neurostimulation with the Bridge, including antipsychotics, narcotics, or benzodiazepines, was also recorded. Patients were instructed to follow up within 1 to 5 days, depending on the clinic, and to leave the device on for the entire 5-day period to prevent the recurrence of symptoms. Any adverse outcome associated with the device was recorded including localized pain, infections, or neurological complaints not related to withdrawal. Informed consent was not obtained due to the retrospective study design.

The main outcome measured was reduction in withdrawal scores as measured by the COW scale. Although the primary outcome of this study was to assess improvement in symptoms during withdrawal from opioids, successful transition to MAT was also investigated in a subset of patients. Those subjects returning to clinic on day 5 post-Bridge placement and receiving their first dose of maintenance medication with the opioid receptor antagonist, naltrexone, were considered to be successfully transitioned.

Statistical analysis was performed with SPSS version 19. Basic descriptive statistics were used for participant demographics. Nonparametric analysis with repeated measures ANOVA was used to evaluate effectiveness in reducing withdrawal scores across all time periods measured. Missing COWS scores were encountered at 20 min (11/73) and at 60 min (2/73). Imputing of missing data was not performed, and analysis was made only with available data since the missing values were considered missing at random. Data were presented as mean (±standard deviation), and $p<0.05$ was considered statistically significant.

Immediately prior to Bridge placement, the majority of patients in this study, 53/73 (72.6%), fell into the moderate withdrawal range, while 16/73 (21.9%) were in the moderately severe range and 4/73 (5.4%) were in the mild range. In the entire cohort, the mean (standard deviation) COWS score prior to Bridge placement was 20.1 (±6.1). The Bridge decreased scores to a mean of 7.5 (±5.9) by 20 minutes (62.7% reduction, $p<0.001$), 4.0 (±4.4) by 30 minutes (80% reduction, $p<0.001$), and 3.1 (±3.4) after 60 minutes (84.6% reduction, $p<0.001$), as shown in FIG. 1. Overall, 73/73 (100%) subject had a reduction in COW scores by 60 minutes with a minimum decrease in at least 36.4%. At 60 minutes 57/73 (78.0%) had withdrawal scores of ≤3. No rescue medications were used in any subject during the first 60 minutes after device placement. During the entire 5-day period, no antipsychotic, narcotic or benzodiazepine medications were given. Thirty eight percent (28/73) of patients received an antiemetic.

A subset of patients also had withdrawal scores recorded 5 days after BRIDGE placement and prior to transitioning to MAT (n=33). For these patients, the average withdrawal score prior to receiving the first dose of naltrexone was 0.6 (97.1% reduction). In the entire cohort of 73 patients, 64 (88.8%) successfully transitioned to MAT after Bridge placement. No adverse events were recorded in any subject during the entire time of neurostimulation with the Bridge.

Example 2

In this Example, all patients involved treated were in the acute phase of heroin or opiate withdrawal as verified by the Clinical Opiate Withdrawal Scale (COWS), a self-report assessment tool for measurement of opiate withdrawal symptoms.

Data was collected on 8 cases. Six had addiction to prescription opiate pain medications and two had heroin addiction. Four were men and four were women and all were Caucasian, with a mean age of 33.2 years (SD=7.1). All patients were in moderate to moderately-severe withdrawal based on COWS scale. The Bridge device was implanted and patients were observed in the clinic for at least one hour before being sent home. Medications were not given in the clinic in order to observe acute Bridge device effects. However patients were given the traditional non-narcotic rescue medications to take at home per request.

Pre-post COWS data were available for 7/8 patients (one missing post-test). The pre-test mean COWS of 21.9 (SD=5.5) was significantly reduced at post-test to 6.1 (SD=5.2), t(6)=5.5, p=0.0015. However, the post-test for one of these patients was obtained the following day. Of the 6 patients for whom COWS data were obtained in clinic, after a mean interval of 32.5 minutes (SD=14.7), mean COWS scores were 23.1 (SD=5.1) at pre-test and 5.9 (SD=5.6) at post-test, t(5)=5.7, p=0.0024. Time to Vivitrol treatment data were available for 7/8 patients (one pending): 4/7 patients (57%) transitioned to Vivitrol in less than 7 days (mean=3.1 days, SD=0.8). The remaining 3 patients were non-compliant with follow-up, resulting in times to Vivitrol of 12, 28, and 140 days. Clinical questioning also indicated that, in addition to significant reduction in COWS scores, patients experienced an improvement of overall mood, decreased sense of distress, and reduction of non-pain symptoms such as goose pimples, rhinorrhea, and restlessness (consistent with stimulation of the para-sympathetic tone). There were no adverse effects associated with the device.

The Bridge device was associated with a significant reduction in opiate withdrawal symptoms. Without intending to be bound by theory, since heroin or opiate withdrawal is a combination of opiate receptor dysfunction and a hyperactive sympathetic nervous system, the Bridge device is believed to stimulate para-sympathetic activity via auricular neuro-vascular bundles containing cranial Nerve's V, XII, IX and X, and localized cervical nerves reducing hyper-excitability motor states associated with adrenergic tone as well as stimulating endogenous endorphins to relieve pain symptoms associated with opiate withdrawal. The average time of the reduction of the COWS scores of 32.5 minutes in this Example may be the result of the nucleus tractus solitarius (NTS) relaying signals to the amygdala and the rostral ventral medulla (RVM) and associated spinal wind-up.

Example 3

This Example investigated the intracranial hemodynamic effect of peri-auricular PENFS. For this study the Electro Accupuncture Device (EAD), Innovative Health Solutions, INC, Versailles, Indiana, was used. The treatment protocol produced significant changes in cerebral hemodynamics as a result of direct cranial nerve stimulation as detected by Transcranial Doppler ultrasonography.

The EAD was powered by 3 1V batteries. After activation the device produced a neuro-modulating signal ranging from 1-10 kQ in intervals of 100 ms, a bipolar impulse width of 1 ms with a duty cycle of 2 hr duty/2 hr rest for a total of 120 hours.

A single 10-minute percutaneous neuromodulating stimulation was performed on a cohort of 12 healthy adult patients during a 3-week span. The cohort, ages 19-64, were randomly recruited. The subjects were interviewed individually. Past medical and surgical histories were collected and screened for potentially disqualifying morbidities. All subject's questions were answered to the subject's satisfaction. Informed consents were signed. Patients were appointed individually at the test site. Upon arrival, the subjects were informed of the nature of the study. Prewritten instructions were read to assure uniform understanding of the instructions. After instructions were read, vital signs were taken and recorded.

Statistics for the variables that were measured prior to EAD implantation and TCD ultrasound measurements are presented in Table 1. The data were used to access any clinical indications for potentially disqualifying morbidities.

TABLE 1

| Collected data before TCD ultrasound measurements (N = 12) | | | | | | | | | |
|---|---|---|---|---|---|---|---|---|---|
| | Age | Systolic | Diastolic | Pulse | Temperature | O$_2$ Air | Weight | Height | BMI |
| Mean | 34.6 | 122.5 | 74.6 | 76.6 | 97.9 | 98.4 | 161.0 | 66.8 | 25.8 |
| Median | 24.5 | 124.0 | 76.0 | 78.0 | 97.8 | 99.0 | 154.5 | 66.0 | 25.0 |
| Minimum | 19.0 | 104.0 | 62.0 | 56.0 | 97.2 | 93.0 | 125.8 | 63.0 | 20.0 |
| Maximum | 64.0 | 148.0 | 88.0 | 92.0 | 98.5 | 100.0 | 220.0 | 71.0 | 33.0 |
| Std. Dev | 16.9 | 15.0 | 8.0 | 9.8 | 0.4 | 2.1 | 30.2 | 2.4 | 3.9 |

Each subject was placed on an exam table in the supine position. For each subject, the chosen ear was disinfected with a 70% isopropyl alcohol pad and left undisturbed for 10 minutes.

After 10 minutes, a baseline TCD assessment of hemodynamics of the middle cerebral, anterior cerebral, posterior cerebral, basilar, in vertebral arteries was performed. Each TCD ultrasound assessment involved measuring the blood flow (mean, peak systolic, and end diastolic) velocities and the downstream cerebral resistance using Gosling's pulsatility index (PI) and Pourcelots resistivity index (RI). The mean velocity, peak systolic velocity, end diastolic velocity (Edv), PI and RI are designated as "Pre-mean", "Pre-Peak", "Pre-Edv", "Pre-PI" and "Pre-RI" for the anterior cerebral artery (ACA), the middle cerebral artery (MCA), and the posterior cerebral artery (PCA).

Next, a NSS sham Device, which had no batteries and percutaneous needles removed, was then placed according to protocol. Before application of the device, the serial number and bar code of the device was recorded. Each patient was placed in the supine position and left undisturbed for 10 minutes. Thereafter, the flow in the transcranial arterial branches was measured using a TCD ultrasound and recorded. The mean velocity, peak systolic, end diastolic velocity, PT and RI values are respectively presented as "Sham-mean", "Sham-Peak", "Sham-Edv", "Sham-PI" and "Sham-RI" for the ACA, MCA, and PCA. The sham device was then removed and disposed.

Next, the subject was left undisturbed for 10 minutes before an active NSS device was placed in a similar way as the shame device. Thereafter, the activated NSS device was implanted according to protocol. Following 10 minutes of NSS device activation, a TCD ultrasound assessment of hemodynamics of the arterial branches performed as previously indicated. The mean velocity, peak systolic velocity, end diastolic velocity, PI and RI data are respectively presented as "Tx-mean", "Tx-Peak", "Tx-Edv", "Tx-PI" and "Tx-RI" for the ACA, MCA, and PCA.

The mean baseline flow in the ACA was found to be 37.3±7.3 cm/s (mean±standard deviation). Upon activation, the mean flow was 46.5±8.1 cm/s. The mean PI and RI before activation were both ≤1.0±0.1, but decreased to 0.8±0.1 and 0.6±0.1 upon activation, respectively.

The baseline mean flow in the PCA was found to 35.6±4.9 cm/s. After implantation of the active NSS device, the mean flow rate rose to 36.0±3.9 cm/s. The baseline PI and RI were 1.0±0.2 and 0.6±0.1, respectively. When an active NSS device was implanted, both the mean PI and RI remained almost unchanged.

The mean MCA baseline flow was found to be 53.1±9.3 cm/s, and 59.4±11.8 cm/s after the active NSS device was implanted. Even after activation, the PI and RI remain almost constant at 0.9±0.2 and 0.6±0.1.

Based on a 2-tailed independent sample tests (p=0.05), the ACA, PCA, and MCA data was tested for correlation. The following variables were statistically significantly and positively correlated (p<0.05): Pre-Edv-ACA and Pre-Mean-ACA (p=0.01, r=0.838); TX-PI-PCA and TX-RI-PCA (r=0.98). The TX-PI-ACA significantly statically positively correlated to all MCA (PI, RI, Mean, Peak, EDV). The Peak-ACA and Mean-ACA were negatively correlated to both PI and RI. The Pre-Mean-ACA, Sham-Mean ACA and the TX-Mean values are weakly negatively correlated to PI-MCA and RI-MCA.

The ACA, PCA and MCA data was tested for any significant differences in variables due to differences in treatments using paired samples t-test (5% Significance level). Paired means that were statistically significantly different are presented in Table 2.

TABLE 2

Paired samples test indicating statistically significant differences (p < 0.05) between the paired means. Upper and lower limits were calculated at 95% confidence level.

|  | Mean | Std. Dev. | Lower | Upper | t | p-value |
|---|---|---|---|---|---|---|
| Pre_ACA - Tx_ACA | −8.675 | 10.2426 | −15.183 | −2.1672 | −2.934 | 0.014 |
| pre_Peak_ACA - Sham_Peak_ACA | −10.8317 | 11.7884 | −18.322 | −3.3417 | −3.183 | 0.009 |
| Pre_Edv_ACA - Sham_Edv_ACA | −6.863 | 5.3084 | −10.236 | −3.4902 | −4.479 | 0.001 |
| Pre_PI_ACA - Sham_PI_ACA | 0.0931 | 0.0885 | 0.0368 | 0.1494 | 3.642 | 0.004 |
| Pre_PI_ACA - Tx_PI_ACA | 0.1031 | 0.1568 | 0.0034 | 0.2027 | 2.276 | 0.044 |
| Pre_RI_ACA - Sham_RI_ACA | 0.0243 | 0.0317 | 0.0041 | 0.0444 | 2.651 | 0.023 |
| pre_Peak_PCA - Sham_Peak_PCA | 6.9167 | 7.8313 | 1.9409 | 11.8924 | 3.060 | 0.011 |
| pre_Peak_MCA - Tx_Peak_MCA | −7.7106 | 10.3095 | −14.261 | −1.1603 | −2.591 | 0.025 |
| Pre_Edv_MCA - Tx_Edv_MCA | −3.9962 | 5.4508 | −7.4595 | −0.5330 | −2.540 | 0.027 |

EAD application changed the mean hemodynamic flow in the cerebral arteries, increasing by 1-19%, while the PI and RI values decreased by 2-11% from the baseline. Therefore, this Example demonstrates an increase in cerebral perfusion by decreasing resistance (decrease PI and RI) to outflow, and a significant increase in mean flow velocity was observed, which was consistent with an increase in cerebral perfusion via cerebral micro-circulatory recruitment. These results support that peri-auricular implantation of the EAD stimulates the cranial nerves anatomically located in the peri-auricular area affecting the extrinsic perivascular innervation, as well as the micro-vascular bed, of the intracranial arteries to decrease flow resistance and increase cerebral perfusion, and trigger autoregulatory mechanisms within the cranium.

Example 4

A group of 5 rats underwent extracellular single-unit recordings from neurons in the central nucleus of the amygdala (CeA). Animals were anesthetized with Urethane (induction, 1.5 g/kg, i.p.; maintenance, 0.05 mg/kg intravenously bolus to maintain plane of anesthesia). Physiological parameters including respiratory rate, heart rate and core body temperature (kept at 37° C.) were continuously monitored. Each animal was mounted in a stereotaxic frame and a small unilateral craniotomy was made to allow for the insertion of the recording electrode. Single-unit recordings from neurons were made with glass-insulated carbon filament electrodes (4-6 MΩ). The following stereotaxic coordinates were used: 2.2 to 3.1 caudal to bregma, 3.8 to 4.2 lateral to midline, depth 6.5 to 8.0. The action potentials were amplified through a low-noise AC differential amplifier (model 3000; AM Systems) and continuously monitored and displayed on an oscilloscope. A dual window discriminator (modelDDIS-1; BAK Electronics) was used to discriminate the action potentials and to convert the signal to a rectangular TTL pulse. The frequency of TTL pulses was counted on-line by using the Spike 2/CED 1401 data acquisition system (Cambridge Electronic Design). Action potentials and blood pressure were recorded on-line. After the experiments, data were analyzed using the Wave-Mark analysis method of the Spike 4 software (Cambridge Electronic Design) to distinguish individual action potentials.

In each animal, background and evoked activity of only one neuron was recorded from the right amygdala. An individual neuron was identified by its background activity and responses to brief search stimuli, which included compression of deep tissue (left paw) with a consistent force using Von Frey filaments. In each experiment, one amygdala neuron that responded to paw compression was selected and recorded. The background activity in the absence of any intentional stimulation was recorded for 5 min. Following the baseline recording, a 30 s compression of the paw was applied twice with the same Von Frey filament (190 mN) 5 min apart. After recording two compressions, the Bridge device was connected to the ear on the ipsilateral side and left undisturbed for 15 minutes. The baseline firing of the neuron and response to compression of the paw was again recorded.

Statistical analysis was performed using SigmaStat (V2.03, SPSS Inc, Chicago, IL). Baseline firing and response of the neurons to paw pinch was measured as action potential counts over 30 sec compression of the paw and were analyzed using one-way repeated.

Figure 2:
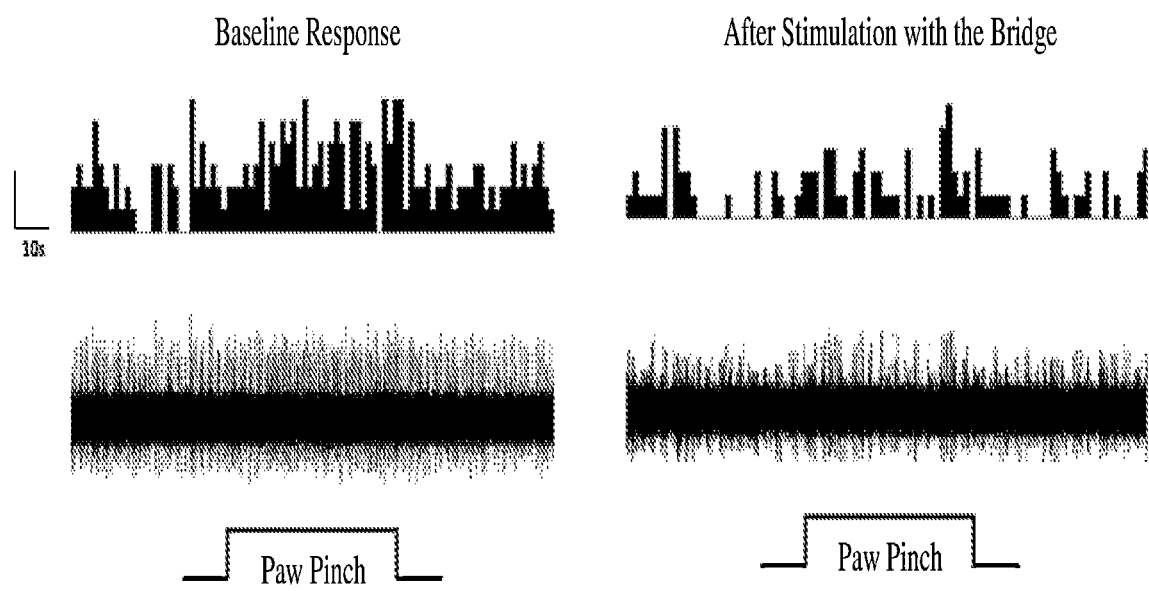
FIG. 2 shows a response of an amygdala neuron before and after auricular stimulation.

Extracellular recordings from amygdala neurons were made in 5 rats. A total of 5 neurons that responded to noxious stimuli (compression) of the hind paw were recorded. All neurons were classified as excitatory with cutaneous receptive fields mainly in the trunk and plantar surface of the paw. A typical response of an amygdala neuron before and after auricular stimulation is shown in FIG. 2, where the top trace shows response as a frequency histogram with 1 s bin width, the middle trace is neuron action potential, and the bottom trace is pay pinch duration.

Prior to auricular stimulation, the mean spontaneous firing of the neurons was 1.15±0.36 imp/sec with an excitatory response to 3.05±0.46 after paw pinch (190 mN). There was a 52% decrease in the spontaneous firing of the neurons after just 15 minutes of auricular stimulation with the Bridge (0.56±0.21 imp/sec). Similarly, the response to compression of the paw was decreased by approximately 66% after auricular stimulation (1.04±0.29 imp/sec) (p<0.05).

Example 5

The incidence of clinically observed bleeding, localized dermatitis and infections at the implantation sites of the electrode/needle arrays, dermatitis at the site of the generator, and patient syncope was quantified. A total of 1207 Neuro-Stem System (NSS), Innovative Health Solutions, INC, Versailles, Indiana, devices, each producing up to 16 percutaneous punctures, for a total of 19312 punctures were monitored for adverse effects, based on retrospective chart audits conducted at 6 clinical facilities over a one-year period.

All patients from the 6 participating centers, who qualified within accepted clinical guidelines, for placement of the NSS were included in this study. Both male and female patients, aged 16 to 70 years, were included in the study. Licensed clinicians were asked to retrospectively review their charting for the outlined adverse patient observations.

The six centers, which were from a wide geographic and interdisciplinary background performed a retrospective chart audit for the preceding 12 months to ascertain the incidence of specified adverse reactions to placement of a total of 1207 NSS devices. Each device had four electrode arrays consisting of 4 needles which were percutaneously implanted into the dorsal or ventral aspect of the external ear for a total of 16 percutaneous punctures per application. The result is a total cohort of 19,312 percutaneous punctures. Data from four different categories was collected:

Bleeding at any puncture site
Dermatitis at any puncture site
Dermatitis at the generator attachment site
Syncope at time of implantation The data on discomfort upon insertion of the electrodes from six different treatment centers is presented in Table 3. Out of a total 19312 punctures, 10 episodes of bleeding and 11 episodes of localized dermatitis were observed at the electrode, respectively. No incidences of syncope (fainting) or infection were observed. There were no reported incidences of syncope in this cohort. This report of findings supports a classification of minimal risk.

TABLE 3

Number of NSS device placements and the reported number of incidences of bleeding, dermatitis, severe pain, and syncope from five different treatment centers.

| | Center A | Center B | Center C | Center D | Center E | Center F |
|---|---|---|---|---|---|---|
| NSS devices | 144 | 141 | 67 | 614 | 151 | 90 |
| Bleeding | 2 | 2 | 0 | 5 | 1 | 1 |
| Dermatitis | 2 | 2 | 0 | 6 | 1 | 0 |
| Severe pain | 0 | 0 | 0 | 2 | 0 | 0 |
| Syncope | 0 | 0 | 0 | 0 | 0 | 0 |

Example 5

Rats were anesthetized with an initial dose of urethane (induction, 1.5 g/kg, i.p) and maintained by bolus dosing through the right femoral vein (0.05 mg/kg). The left carotid artery was also cannulated to monitor blood pressure. Following tracheal intubations, the rats were paralyzed with an initial dose of gallamine triethiodide (10 mg·kg$^{-1}$ i.v., Flaxedil) and mechanically ventilated with room air (~60 strokes·min$^{-1}$). Subsequent doses of gallamine triethiodide (5 mg·kg$^{-1}$·h$^{-1}$) were given as needed to maintain paralysis. The body temperature was kept within physiological range (36-37° C.) with an overhead lamp. The rats were placed in a stereotaxic head holder and the thoraco-lumbar (T13-L2) spinal cord was exposed by laminectomy. After removal of the dura membrane, a 1-2 cm saline-soaked gelatin sponge (Gelfoam, Pharmacia Upjohn Company, MI USA) was employed to cover the exposed spinal cord segment. The skin was reflected laterally to make a pool for agar solution that was allowed to cool to 38° C. prior to pouring. The agar was allowed to harden and the dorsal surface of the spinal cord was exposed by removing a cubical slice of agar with a scalpel blade. The exposed surface of the spinal cord was covered with warm mineral oil (37° C.).

Extracellular single-unit recordings were performed on two rats from the lumbar (L1-L2) spinal segments using glass-insulated, carbon filament electrodes. The placement of the electrode was 0.1-0.5 mm lateral from the spinal midline and 0.6-1.8 mm ventral from the dorsal surface. The action potentials were amplified through a low-noise AC differential amplifier (model 3000; A-M Systems) and continuously monitored and displayed on an oscilloscope. A dual window discriminator (model DDIS-1; BAK Electronics) was used to discriminate the action potentials and to convert it to rectangular TTL pulse. The frequency of TTL pulses was counted online by using the Spike2/CED 1401 data acquisition system (Cambridge Electronic Design). Action potentials and blood pressure were recorded. Post experiments, data were analyzed using the Wave-Mark analysis method of the Spike 4 software (Cambridge Electronic Design) to distinguish individual action potentials.

The spontaneous neuronal activity was recorded for each neuron followed by recording of responses to noxious pinch of the paw using Von Frey filament (190 N) for 10 seconds. After obtaining the baseline response, the Bridge device was attached to the contralateral ear. After 15 minutes of stimulation, the baseline firing and response to paw pinch was again recorded.

Figure 3:
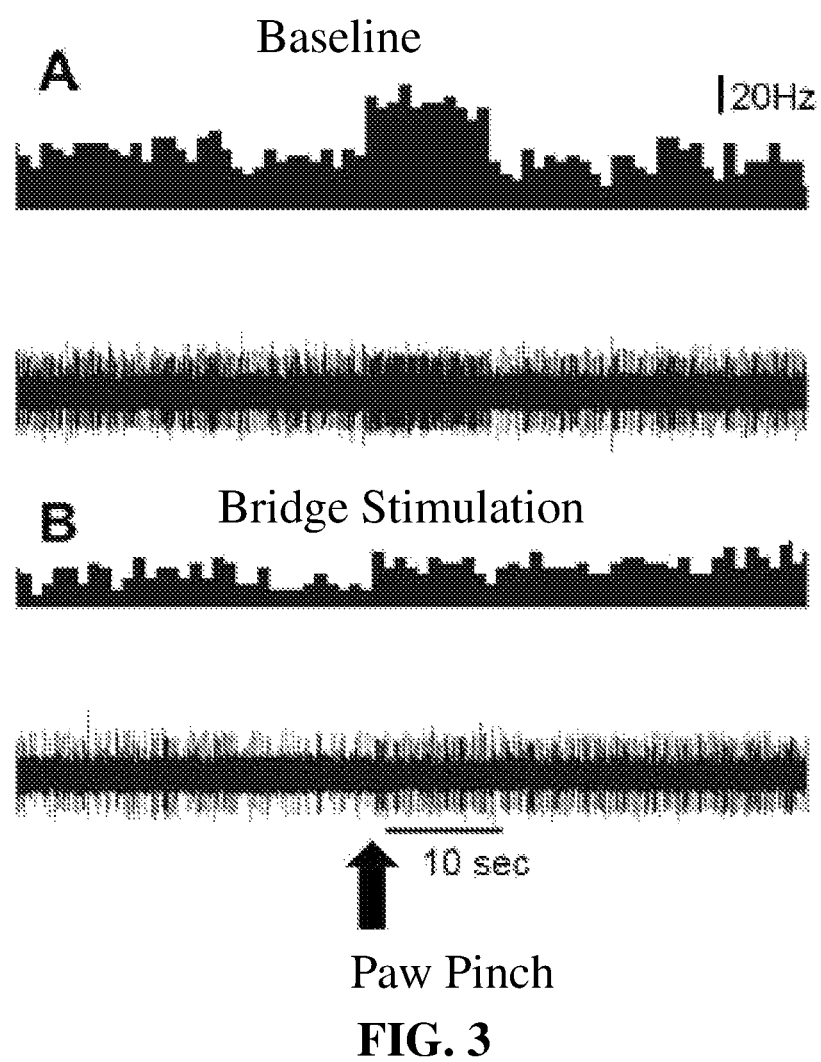
FIG. 3 shows a response of a lumbar spinal neuron before and after auricular stimulation.

One neuron from each animal (n=2) that responded to compression of the hind paw were recorded. All neurons were classified as excitatory and had cutaneous receptive fields mainly in the ipsilateral rump area. An example of one spinal neuron recorded before and after stimulation with the Bridge device is shown in FIGS. 3A and 3B, respectively. Each frequency histogram in the FIGS. 3A and 3B has a 1 s bin width.

Following stimulation with the Bridge, there was a decrease in the spontaneous baseline firing of the neurons (4.6±0.21 imp/sec) compared to pre-stimulation (9.5±0.43 imp/sec). Similarly, firing of the neurons in response to pinching of the paw was much lower after auricular stimulation (7.7±0.24 imp/sec) compared to the pre-stimulation response (15.8±1.43 imp/sec).

Example 6

This Example evaluated the efficacy, safety, and tolerability of a 3 week trial of Neuro-Stem System (NSS), Innovative Health Solutions, INC, Versailles, Indiana vs. placebo in children with FAPDs.

This study was a double-blind, randomized, placebo-controlled study that included children ages 11-18 years who satisfied criteria for a FAPD based on the Rome III version of the Questionnaire on Pediatric Gastrointestinal Symptoms (QPGS) and weekly symptoms as assessed by the provider for any of the four FAPDs including irritable bowel syndrome (IBS), functional dyspepsia, functional abdominal pain-not otherwise specified (FAP-NOS), and abdominal migraine. Subjects were required to have an average daily pain rate ≥3 out of 10 (on a 0 to 10-point numerical rating scale for worst abdominal pain the week prior to starting the trial). The primary end point was determined using the Pain Frequency-Severity-Duration (PFSD) scores. The PFSD is a validated pain tool for children designed to incorporate multiple aspects of the pain experience with 3 major weekly scores: usual pain (0-10), worst pain (0-10) and number of days in pain (0-7). Groups were compared for improvement in worst pain over the 3 week treatment and the PFSD composite score for all 3 measures. The composite score was derived by multiplying the number of days of pain, the level of usual pain, and the level of worst pain and then dividing the product by 10. The highest possible score was 70. The key secondary end point percentage of patients who achieved a clinical response at week 3, defined as a patient who reported a decrease of ≥30% in weekly worst abdominal pain from baseline. This primary outcome was based on the FDA recommendation for IBS in adults and the ROME foundation pediatric subcommittee on clinical trials in children. Also, the proportion of patients who had global improvement of at least +2 in the weekly symptom response scale (SRS) was used as a secondary outcome. Several studies have demonstrated that when using 7-point scale response options in disease-specific measures, a change in score of 0.5 represents the minimally important difference. A change of 1.0 is considered a moderate change in quality of life, and a change in score greater than 1.5 is likely to represent a large change.

For analysis of the PFDS scores, 30% improvement in pain, and symptoms response scale, the Fisher's exact test was used to compare categorical variables and the Mann-Whitney test was used to compare continuous variables. Time, treatment group, and time ×treatment group were predictors. All data are presented as mean±S.E.M. Comparison between groups was based on intention-to-treat (ITT) principle. A p-value <0.05 was considered statistically significant.

In the study period, 115 children with abdominal pain due to FAPDs were enrolled and assigned to either neurostimulation (n=57) or sham device (n=47). Two patients were excluded due to a change in diagnosis after starting the study. One patient was found to have *helicobacter* infection with gastric ulcers and the second patient was found to have eosinophilic esophagitis on endoscopy. Nine patients withdrew from the study after starting due to aesthetic reasons regarding the device. Median worst pain at baseline was very similar between placebo and treatment group. Over time, a greater improvement in worst pain scores from baseline was seen in the group with active treatment. This result was significant at all 3 weeks measured compared to placebo (p<0.001). At week 3, the placebo group had worse pain with a median of 7 compared to treatment group 5 (p<0.001).

PFSD composite scores at baseline (22.8) were similar to those in the treatment group (24.5). Composite scores in the treatment group decreased at week 1(12.4), week 2 (12.0) and week 3 (8.4) (p<0.001). No change was seen from baseline in the placebo group in weeks 1 through 3 (14.4, 14.7 and 15.2, respectively). At week 3, placebo group had worse total score with a median of 15.2 compared to the treatment group 8.4 (p<0.005).

Using a ≥30% reduction in worst pain as a responder threshold, 60% of patients in the active treatment group improved compared to 22% in the control group at week 3 compared to baseline (p<0.001). Similarly, by week 3, 57% of patients in the treatment group had at least a 30% improvement in usual (average) pain scores from baseline compared to 29% in the placebo group (p=0.007).

Subjects rated their symptoms as better, worse or no change based on a 15 point scale: −7 to −1=worse; 0=no change; +1 to +7=better). A score of +2 was considered to be significant improvement in global rating of symptoms. At the end of the 3 week treatment, the placebo group had a median change in score of +1 (−5 to 6). The treatment group was significantly better at the end of 3 weeks with a median score of +3 (−3 to 7) representing a large improvement in global rating of symptoms over placebo (p<0.001).

From the entire cohort, 11 subjects reported side effects in both groups. Six patients reported ear discomfort, (4 of these patients had active device and 2 had sham device). Three patients had adhesive reactions, 1 patient developed dizziness and nausea after device placement (active device). There was 1 patient in the placebo group who had an episode of syncope prior to placement of device. This was later determined to be related to needle phobia.

Treatment with Neuro-Stim device significantly improved worst pain and composite pain scores from baseline in all 3 weeks measured. There was also a improvement in the treatment group compared to placebo using the responder definition of ≥30% improvement in weekly pain. Overall global symptoms improvement was significantly better in those with active treatment compared to placebo.

We claim:

1. A method of treating anxiety comprising:
altering response characteristics of amygdala neurons and lumbar neurons, wherein the altering step includes:
stimulating a cranial nerve with an electrical signal.

2. The method of claim 1, wherein the cranial nerve is selected from the group consisting of cranial nerve V, cranial nerve VII, cranial nerve IX, cranial nerve X, and branches of greater and lesser occipital nerves thereof and their associated neurovascular bundles.

3. The method of claim 2, wherein the cranial nerve is cranial nerve V.

4. The method of claim 2, wherein the cranial nerve is cranial nerve V and associated neurovascular bundles.

5. The method of claim 2, wherein the cranial nerve is cranial nerve VII.

6. The method of claim 2, wherein the cranial nerve is cranial nerve VII and associated neurovascular bundles.

7. The method of claim 2, wherein the cranial nerve is cranial nerve IX.

8. The method of claim 2, wherein the cranial nerve is cranial nerve IX and associated neurovascular bundles.

9. The method of claim 2, wherein the cranial nerve is cranial nerve X.

10. The method of claim 2, wherein the cranial nerve is cranial nerve X and associated neurovascular bundles.

11. The method of claim 2, wherein the cranial nerve is branches of greater and lesser occipital nerves.

12. The method of claim 2, wherein the cranial nerve is branches of greater and lesser occipital nerves and associated neurovascular bundles.

* * * * *